United States Patent
Mihalik et al.

(10) Patent No.: US 7,727,191 B2
(45) Date of Patent: Jun. 1, 2010

(54) COMPLIANT BALLOON CATHETER

(75) Inventors: Teresa Ann Mihalik, Montréal (CA);
Jean-Luc Pageard, Montréal (CA);
John W. Lehmann, Wayland, MA (US)

(73) Assignee: Medtronic Cryocath LP, Toronto, Ontario (CA)

( * ) Notice: Subject to any disclaimer, the term of this patent is extended or adjusted under 35 U.S.C. 154(b) by 996 days.

(21) Appl. No.: 11/129,210

(22) Filed: May 13, 2005

(65) Prior Publication Data

US 2006/0270982 A1    Nov. 30, 2006

(51) Int. Cl.
*A61M 29/00*    (2006.01)
*A61F 7/12*    (2006.01)

(52) U.S. Cl. .................................. 604/113; 604/101.01

(58) Field of Classification Search .................. 604/113, 604/101.01, 101.02, 101.03, 103
See application file for complete search history.

(56) References Cited

U.S. PATENT DOCUMENTS

| | | | |
|---|---|---|---|
| 5,342,305 A * | 8/1994 | Shonk | 604/101.02 |
| 5,358,487 A | 10/1994 | Miller et al. | |
| 5,447,497 A * | 9/1995 | Sogard et al. | 604/101.02 |
| 5,843,027 A | 12/1998 | Stone et al. | |
| 5,868,735 A * | 2/1999 | Lafontaine | 606/21 |
| 5,964,778 A | 10/1999 | Fugoso et al. | |
| 5,971,979 A | 10/1999 | Joye et al. | |
| 5,980,486 A | 11/1999 | Enger | |
| 6,012,457 A | 1/2000 | Lesh | |
| 6,024,740 A | 2/2000 | Lesh et al. | |
| 6,036,697 A | 3/2000 | DiCaprio | |
| 6,164,283 A | 12/2000 | Lesh | |
| 6,179,810 B1 | 1/2001 | Wantink et al. | |

(Continued)

FOREIGN PATENT DOCUMENTS

WO    0207628 A2    1/2002

(Continued)

OTHER PUBLICATIONS

Avitall, B., et al., *New Cryotechnology for Electrical Isolation of the Pulmonary Veins*, Journal of Cardiovascular Electrophysiology, vol. 14, No. 3, Mar. 2003, pp. 281-286.

*Primary Examiner*—Kevin C Sirmons
*Assistant Examiner*—Andrew M Gilbert
(74) *Attorney, Agent, or Firm*—Christopher & Weisberg, P.A.

(57) ABSTRACT

A catheter includes a first expandable membrane having a first pressurization limit and a second expandable membrane, having a second pressurization limit, wherein the second pressurization limit is greater than the first pressurization limit, the first expandable membrane defines a cooling chamber, the second expandable membrane being disposed around the first expandable membrane to define an junction therebetween. The catheter includes a coolant injection lumen in fluid communication with the at least one fluid inlet port and the cooling chamber, and a primary coolant return lumen in fluid communication with the at least one fluid outlet port and the cooling chamber. The coolant injection tube, the cooling chamber, and the primary coolant return lumen define a first fluid pathway. The catheter further includes a secondary coolant return lumen in fluid communication with the at least one fluid outlet port and the junction. The junction and the secondary coolant return lumen define a second fluid pathway. The catheter provides a fail-safe feature by selecting the appropriate first and second pressurization limits for the first and second expandable membranes.

10 Claims, 2 Drawing Sheets

U.S. PATENT DOCUMENTS

| | | | |
|---|---|---|---|
| 6,179,827 B1 | 1/2001 | Davis et al. | |
| 6,233,491 B1 | 5/2001 | Kordis et al. | |
| 6,237,604 B1 | 5/2001 | Burnside et al. | |
| 6,241,754 B1 | 6/2001 | Swanson et al. | |
| 6,245,064 B1 | 6/2001 | Lesh et al. | |
| 6,254,599 B1 | 7/2001 | Lesh et al. | |
| 6,290,696 B1 | 9/2001 | Lafontaine | |
| 6,305,378 B1 | 10/2001 | Lesh | |
| 6,325,797 B1 | 12/2001 | Stewart et al. | |
| 6,344,045 B1 | 2/2002 | Lim et al. | |
| 6,355,029 B1 * | 3/2002 | Joye et al. | 606/21 |
| 6,387,092 B1 | 5/2002 | Burnside et al. | |
| 6,416,511 B1 | 7/2002 | Lesh et al. | |
| 6,432,102 B2 | 8/2002 | Joye et al. | |
| 6,471,694 B1 | 10/2002 | Kudaravalli et al. | |
| 6,495,090 B1 | 12/2002 | Wilkins | |
| 6,502,576 B1 | 1/2003 | Lesh | |
| 6,514,245 B1 | 2/2003 | Williams et al. | |
| 6,514,249 B1 | 2/2003 | Maguire et al. | |
| 6,517,533 B1 | 2/2003 | Swaminathan | |
| 6,578,579 B2 | 6/2003 | Burnside et al. | |
| 6,595,988 B2 * | 7/2003 | Wittenberger et al. | 606/21 |
| 6,602,276 B2 | 8/2003 | Dobak, III et al. | |
| 6,645,234 B2 | 11/2003 | Evans et al. | |
| 6,648,878 B2 | 11/2003 | Lafontaine | |
| 6,648,879 B2 * | 11/2003 | Joye et al. | 606/21 |
| 6,648,883 B2 | 11/2003 | Francischelli et al. | |
| 6,652,515 B1 | 11/2003 | Maguire et al. | |
| 6,659,981 B2 | 12/2003 | Stewart et al. | |
| 6,666,858 B2 | 12/2003 | Lafontaine | |
| 6,685,732 B2 | 2/2004 | Kramer | |
| 6,702,811 B2 | 3/2004 | Stewart et al. | |
| 6,740,104 B1 | 5/2004 | Solar et al. | |
| 6,989,009 B2 * | 1/2006 | Lafontaine | 606/20 |
| 7,052,510 B1 * | 5/2006 | Richter | 623/1.11 |
| 7,056,274 B2 * | 6/2006 | Apple et al. | 600/3 |
| 7,291,144 B2 * | 11/2007 | Dobak et al. | 606/22 |
| 2002/0007180 A1 | 1/2002 | Wittenberger et al. | |
| 2002/0045894 A1 | 4/2002 | Joye et al. | |
| 2002/0128636 A1 | 9/2002 | Chin et al. | |
| 2003/0199861 A1 | 10/2003 | Lafontaine | |
| 2004/0034344 A1 | 2/2004 | Ryba | |
| 2004/0073203 A1 | 4/2004 | Yu et al. | |
| 2004/0173935 A1 | 9/2004 | Lim et al. | |
| 2004/0243119 A1 | 12/2004 | Lane et al. | |
| 2006/0173526 A1 * | 8/2006 | Richter | 623/1.11 |
| 2006/0211983 A1 * | 9/2006 | Davidson et al. | 604/96.01 |
| 2007/0167973 A1 * | 7/2007 | Stupecky et al. | 606/192 |
| 2009/0299356 A1 * | 12/2009 | Watson | 606/21 |

FOREIGN PATENT DOCUMENTS

| | | |
|---|---|---|
| WO | WO 02/07628 A | 1/2002 |
| WO | 03088857 A2 | 10/2003 |
| WO | WO 03/088857 A | 10/2003 |

* cited by examiner

COMPLIANT BALLOON CATHETER

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates medical systems, and in particular to methods and systems for improving the safety of cryotreatment medical systems.

BACKGROUND OF THE INVENTION

The experimental use of fluids with low operating temperatures, or cryogens, continues in the medical and surgical field. Of particular interest are the potential use of catheter based devices, which employ the flow of cryogenic working fluids therein, to selectively freeze, or "cold-treat", targeted tissues within the body. Catheter based devices are desirable for various medical and surgical applications in that they are relatively non-invasive and allow for precise treatment of localized discrete tissues that are otherwise inaccessible. Catheters may be easily inserted and navigated through the blood vessels and arteries, allowing non-invasive access to areas of the body with relatively little trauma.

Catheter-based ablation systems are known in the art. A cryogenic device uses the energy transfer derived from thermodynamic changes occurring in the flow of a cryogen therethrough to create a net transfer of heat flow from the target tissue to the device, typically achieved by cooling a portion of the device to very low temperature through conductive and convective heat transfer between the cryogen and target tissue. The quality and magnitude of heat transfer is regulated by the device configuration and control of the cryogen flow regime within the device.

A cryogenic device uses the energy transfer derived from thermodynamic changes occurring in the flow of a refrigerant through the device. This energy transfer is then utilized to create a net transfer of heat flow from the target tissue to the device, typically achieved by cooling a portion of the device to very low temperature through conductive and convective heat transfer between the refrigerant and target tissue. The quality and magnitude of heat transfer is regulated by device configuration and control of the refrigerant flow regime within the device.

Structurally, cooling can be achieved through injection of high-pressure refrigerant through an orifice. Upon injection from the orifice, the refrigerant undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to the desired temperature.

Once refrigerant is injected through an orifice, it may be expanded inside of a closed expansion chamber, which is positioned proximal to the target tissue. Devices with an expandable membrane, such as a balloon, are employed as expansion chambers. In such a device, refrigerant is supplied through a catheter tube into an expandable balloon coupled to such catheter, wherein the refrigerant acts to both: (i) expand the balloon near the target tissue for the purpose of positioning the balloon, and (ii) cool the target tissue proximal to the balloon to cold-treat adjacent tissue.

The operation of such a device for therapeutic purposes requires that the coolant be contained within the catheter at all times, lest a leak of coolant enter the body and thereby cause significant harm. Known catheters which employ inflatable balloons often inflate the balloons to relatively high pressures that exceed the ambient pressure in a blood vessel or body lumen. However, to contain the coolant, these catheters generally employ thicker balloons, mechanically rigid cooling chambers, and other similar unitary construction containment mechanisms. These techniques however, lack robustness, in that if the unitary balloon, cooling chamber, or other form of containment develops a crack, leak, rupture, or other critical structural integrity failure, coolant may quickly flow out of the catheter.

It would be desirable to provide an apparatus and method of monitoring and controlling the potential rupture or leakage of a balloon catheter that is adaptable and compatible with various types of balloon ablation catheters.

SUMMARY OF THE INVENTION

The present invention advantageously provides a method and system for improving the safety of a balloon catheter. The method and system allows for providing a "fail safe" operation of the balloon catheter.

The present invention advantageously provides an enhanced safety catheter that has a proximal end portion and a distal end portion, the proximal end portion defining at least one fluid inlet port and at least one fluid outlet port. The catheter also includes a first expandable membrane having a first pressurization limit and a second expandable membrane, having a second pressurization limit, where the second pressurization limit is greater than the first pressurization limit and the first expandable membrane defines a cooling chamber, where the second expandable membrane is disposed around the first expandable membrane to define an junction therebetween. The catheter may further include a coolant injection lumen in fluid communication with at least one fluid inlet port and the cooling chamber, and a primary coolant return lumen in fluid communication with the at least one fluid outlet port and the cooling chamber. The coolant injection tube, the cooling chamber, and the primary coolant return lumen define a first fluid pathway. The catheter further includes a secondary coolant return lumen in fluid communication with the at least one fluid outlet port and the junction. The junction and the secondary coolant return lumen define a second fluid pathway.

The catheter system may further provide a control unit for controlling the flow of cryogenic fluid to the catheter, and several sensors to monitor various temperatures, flow rates and pressures of the catheter system The catheter provides a fail-safe feature by selecting the appropriate first and second pressurization limits for the first and second expandable membranes.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
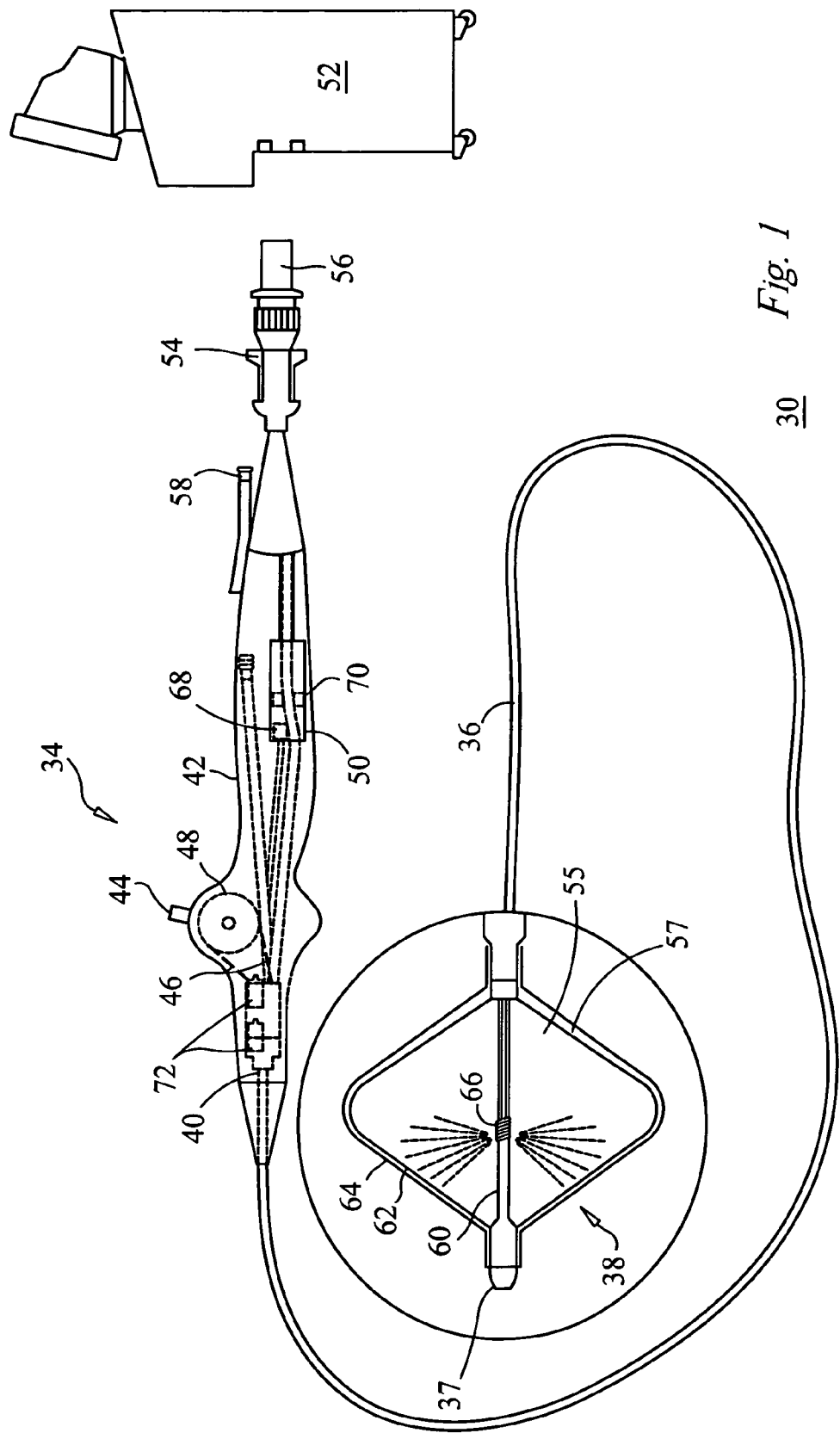
FIG. 1 illustrates a balloon catheter system in accordance with a first embodiment of one aspect of the present invention.

FIG. 1 illustrates an exemplary system 30 for performing cryogenic ablation. The system 30 includes an elongate, highly flexible ablation catheter 34 that is suitable for passage through the vasculature. The ablation catheter 34 includes a catheter body 36 having a distal end 37 with a thermally conductive element 38 at or proximal to the distal end 37. The distal end 37 and the thermally conductive element 38 are shown magnified and are described in greater detail below. The catheter body 36 has a proximal end 40 that is mated to a handle 42 that can include an element such as a lever 44 or knob for manipulating the catheter body 36 and the thermally conductive element 38. In the exemplary embodiment, a pull wire 46 with a proximal end and a distal end has its distal end anchored to the catheter at or near the distal end 37. The proximal end of the pull wire 46 is anchored to an element such as a cam 48 in communication with and responsive to the lever 44. The handle 42 can further include circuitry 50 for identification and/or use in controlling of the ablation catheter 34 or another component of the system 30.

Continuing to refer to FIG. 1, the handle 42 can also include connectors that are matable directly to a cryogenic fluid supply/exhaust and control unit or indirectly by way of one or more umbilicals. In the system illustrated, the handle 42 is provided with a first connector 54 that is matable with a co-axial fluid umbilical (not shown) and a second connector 56 that is matable with an electrical umbilical (not shown) that can further include an accessory box (not shown). In the exemplary system the fluid supply and exhaust, as well as various control mechanisms for the system are housed in a single console 52. In addition to providing an exhaust function for the ablation catheter fluid supply, the console 52 can also recover and/or re-circulate the cooling fluid. The handle 42 is provided with a fitting 58 for receiving a guide wire (not shown) that is passed into a guide wire lumen 60.

Still referring to FIG. 1, the thermally conductive element 38 is shown as a double balloon having a first membrane (e.g., inner balloon) 62 contained or enclosed within a second membrane (e.g., outer balloon) 64, thereby defining an interface or junction 57 between the first and second membranes. The second membrane 64 provides a safeguard to prevent fluid from leaking out of the cooling chamber 55 and into surrounding tissue should the first membrane 62, and therefore the cooling chamber 55, rupture or develop a leak. The junction 57 between the first and second membranes 62, 64 may be substantially under a vacuum, such that the first and second membranes 62, 64 are generally in contact with each other, with little or no open space between them. A coolant supply tube 66 in fluid communication with the coolant supply in the console 52 is provided to release coolant from one or more openings in the tube within the inner balloon 62 in response to console commands and other control input. A vacuum pump in the console 52 creates a low-pressure environment in one or more lumens within the catheter body 36 so that coolant is drawn into the lumen(s), away from the inner balloon 62, and towards the proximal end of the catheter body. The vacuum pump is also in fluid communication with the interface or junction 57 of the inner and the outer balloons 62, 64 so that any fluid that leaks from the inner balloon 62 is contained and aspirated. Still referring to FIG. 1, the handle 42 includes one or more pressure sensors 68 to monitor the fluid pressure within one or both of the balloons, the blood detection devices 70 and the pressure relief valves 72. When coolant is released into the inner balloon 62, the inner and the outer balloon 64 expand to a predetermined shape to present an ablation surface, wherein the temperature of the ablation surface is determined by the material properties of the specific coolant selected for use, such as nitrous oxide, along with the pressure within the inner balloon 62 and the coolant flow rate.

When operating a balloon catheter 34 under positive pressure, it is useful to design a safety feature capable of monitoring the system for leaks or the like. One such safety feature is to shield or envelope the exterior of the pressurized inner balloon 62 with a second outer balloon 64. The second outer balloon 64 can be maintained under vacuum to capture any gas leaks that may be formed in the pressurized inner balloon system 62.

Figure 2:
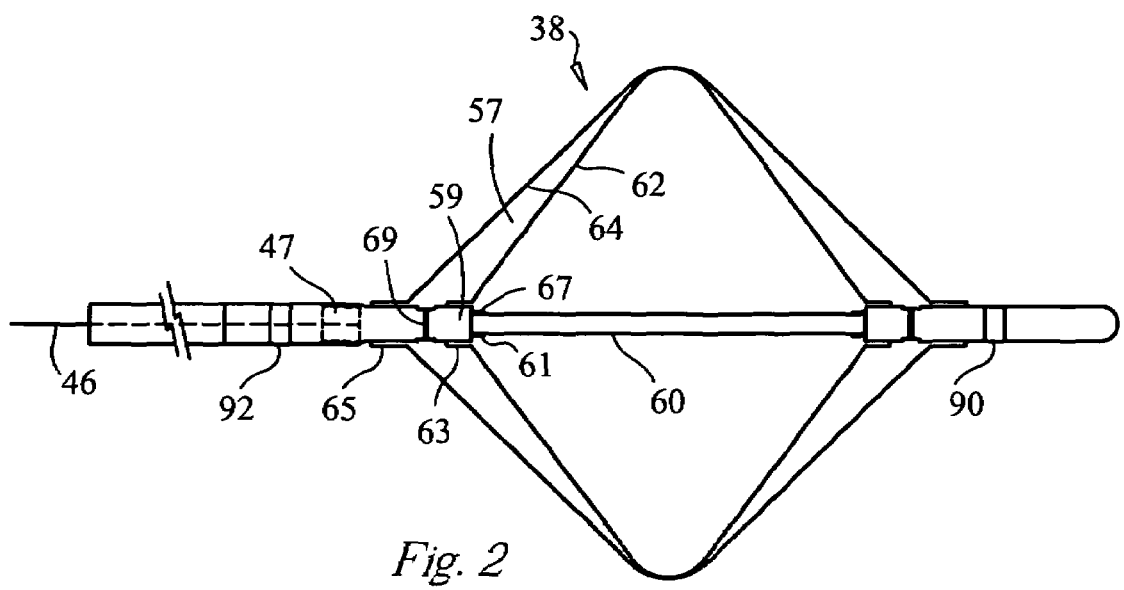
FIG. 2 illustrates an embodiment of a shaft of the balloon catheter system of FIG. 1; and, FIG. 3 illustrates Probability Graphs for the Upper Prediction Band of the Inner Balloon Burst Pressure and the Lower Prediction Band of the Outer Balloon Burst Pressure.

FIG. 2 illustrates an embodiment of a shaft or catheter body 36 of the balloon catheter system 34 of FIG. 1. The catheter body 36 includes a mounting section 59 in communication with the proximal end of thermally conductive element 38. The inner balloon 62 and outer balloon 64 are bonded to the mounting section 59. In this embodiment, the inner balloon 62 and outer balloon 64 are bonded at different locations, which are defined as the inner balloon bond joint 63 and the outer bond joint 65. In addition, several optional sensors are identified including a thermocouple wire 61, and one or more leak detection wires 67 and 69. A pull ring 47 is secured near the proximal end of thermally conductive element 38 and is affixed to the distal end of pull wire 46.

The inner balloon 62 may be designed to insure that it is the weakest point of the balloon catheter 34 and certain to fail before the outer balloon 64. In this case, the inner balloon's role in the catheter 34 is comparable to that of a pressure relief valve or a rupture disc. In general, rupture discs typically are selected based on its so-called "operating ratio" that is defined as the ratio of operating pressure to stamped burst pressure (e.g., the average of the destructive burst tests at the time of manufacture). Moreover, the operating ratio may be used to determine the "pressurization limit" of each balloon. The pressurization limit of a balloon is a function of two elements, the balloon burst pressure or tensile strength and the sealing strength of a balloon bond joint 63, 65 to the catheter body. The inner balloon 62 may be designed with its operating ratio and it pressurization limit based on an acceptable level of risk or probability that the normal or faulty operating pressure of the catheter 34 does not exceed the burst pressure of the inner balloon 62. For example, the inner balloon pressure will vary during different operating conditions, such as during inflation, transition, ablation, thawing, deflection, and the like. In addition, several fault conditions could exist, such as minimum and maximum catheter torquing, blocked vacuum, shaft kinking and the like. One method is to select an inner balloon 62 with a operating ratio such that the lower 99.9% prediction bound of the inner balloon burst pressure does not overlap the upper 99.9% prediction bound of the normal or faulty conditions. The resulting catheter 34 would have a less than one in one million probability of causing an inner balloon burst when the catheter 34 was operating in a normal or fault mode. For example, if the inner balloon pressure range for normal or faulty conditions is found to be between 15 and 30 psia, then an inner balloon burst pressure of 45 psia may provide a 99.9% prediction bound of the inner balloon burst pressure that does not overlap the upper 99.9% prediction bound of the normal or faulty conditions.

Although increasing the thickness of the material, changing the material formulation, or altering the geometry may increase the burst resistance of the inner balloon 62, there are other limiting factors to consider in the designing of balloon catheters 34 used in intracardiac ablations or cryoablations, such as balloon rewrap profile for withdrawal into a sheath, the effective conduction of warm or cold through the balloon layers, and the like. Such factors should be considered in the balloon design, in order to estimate a minimum burst pressure as a balloon design is optimized.

As mentioned above, the inner balloon 62 may function as a pressure relief valve or a rupture disc. Instead of setting the inner balloon burst pressure, the sealing strength of the inner balloon bond joint 63 may be used to act as a pressure relief valve. The sealing strength of inner balloon bond joint 63 may be selected such that it would fail before the burst force rating or pressurization limit of the inner balloon is exceeded. For an outer vacuum system with a rapid response to capture leaks, this would avoid the outer balloon 64 being subject to sudden pressurization due to an inner balloon burst.

An inherent "fail safe" double balloon design strategy is one where even in the case of a catastrophic inner balloon 62 burst, the integrity of the outer balloon 64 would remain intact and the captured gas and/or pressurization and/or loss of vacuum would be used to signal the system 30 to immediately terminate the current application or procedure.

Figure 3:
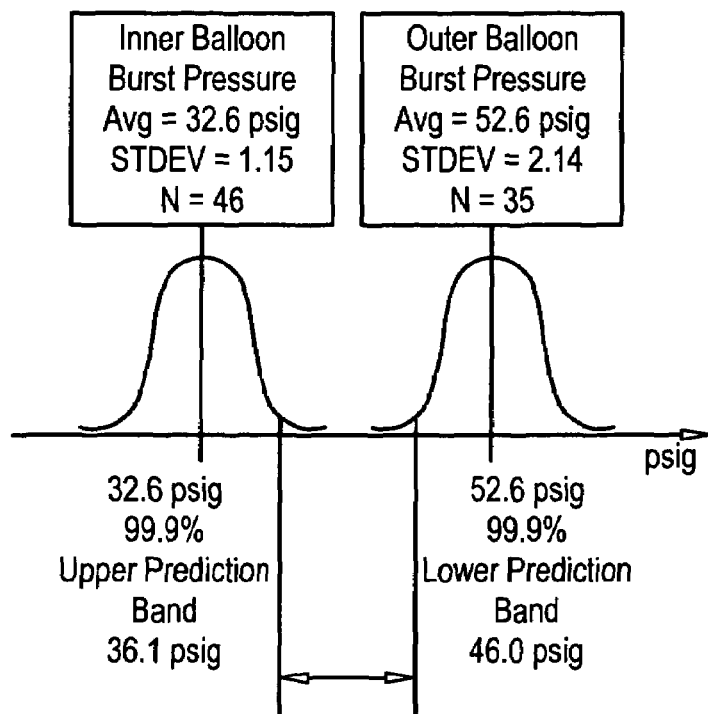

One method is to select a non-compliant outer balloon 64 that is based on an acceptable level of risk or probability that the upper bound of inner balloon burst pressure will not overlap the lower bound of outer balloon burst based on statistical sampling of destructive burst testing. For non-compliant outer balloons 64, the resistance of the outer balloon 64 to an inner burst is based primarily on the burst rating of the balloon itself. For example, FIG. 3 illustrates a probability distribution curve wherein the inner balloon burst pressure has a mean average of 32.6 psig, a standard deviation of 1.15 with a sample size N=46, which results in a 99.9% upper prediction band pressure of 36.1 psig. FIG. 3 also illustrates a probability distribution curve wherein the outer balloon burst pressure has a mean average of 52.6 psig, a standard deviation of 2.14 with a N=35, which results in a 99.9% lower prediction band pressure of 46.0 psig. The resulting catheter 34 would have a less than one in $10^6$ probability that an inner balloon burst would cause an outer balloon burst.

For a compliant outer balloon 64, the resistance of the outer balloon 64 to an inner burst is a complex phenomenon that depends on both the burst rating and the ability of the balloon material to contain the rapid rate of pressure increase by a change in volume or expansion due to compliance. In this case, it is not necessary for the outer balloon 64 to have a burst rating higher than the inner balloon 62. The outer balloon 64 merely needs to effectively expand to absorb the pressure and contain the gas released by an inner balloon burst.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A catheter comprising:
   a proximal end portion and a distal end portion, the proximal end portion defining at least one fluid inlet port and at least one fluid outlet port;
   a first expandable membrane having a first pressurization limit, and a second expandable membrane, having a second pressurization limit, wherein the second pressurization limit is approximately 20 psig greater than the first pressurization limit; wherein the first expandable membrane is coupled to the catheter at an inner bond joint, and the second expandable membrane is coupled to the catheter at an outer bond joint, and wherein the first pressurization limit is determined by the sealing strength of the inner bond joint;
   the first expandable membrane defining a cooling chamber, the second expandable membrane disposed around the first expandable membrane defining a junction between the first and second expandable membranes;
   a coolant injection lumen in fluid communication with the at least one fluid inlet port and the cooling chamber;
   a primary coolant return lumen in fluid communication with the at least one fluid outlet port and the cooling chamber, the coolant injection lumen, the cooling chamber, and the primary coolant return lumen defining a first fluid pathway; and,
   a secondary coolant return lumen in fluid communication with the at least one fluid outlet port and the junction, the junction and the secondary coolant return lumen defining a second fluid pathway.

2. The catheter of claim 1, wherein the first pressurization limit is determined by the tensile strength of the first expandable membrane.

3. The catheter of claim 2, wherein the first pressurization limit is less than the tensile strength of the second expandable membrane.

4. The catheter of claim 1, wherein the first pressurization limit is less than the tensile strength of the first expandable membrane.

5. The catheter of claim 1, wherein the first pressurization limit is less than the tensile strength of the second expandable membrane.

6. The catheter of claim 1, wherein the first pressurization limit is determined by a first operating ratio.

7. The catheter of claim 6, wherein the second expandable membrane has a second operating ratio, and wherein the first operating ratio has an upper bound which will not overlap a lower bound of the second operating ratio.

8. The catheter of claim 2, further comprising a supply of cryogenic fluid in fluid communication with the injection lumen.

9. The catheter of claim 2, further comprising a vacuum source in fluid communication with the secondary coolant return lumen.

10. The catheter of claim 1, wherein the second expandable membrane is a compliant balloon.

* * * * *